United States Patent [19]

Romano

[11] 4,097,676

[45] Jun. 27, 1978

[54] METHOD FOR THE PREPARATION OF AROMATIC URETHANS

[75] Inventor: Ugo Romano, Milan, Italy

[73] Assignee: Anic S.p.A., Palermo, Italy

[21] Appl. No.: 744,109

[22] Filed: Nov. 22, 1976

[30] Foreign Application Priority Data

Dec. 3, 1975 Italy ............................. 29960 A/75

[51] Int. Cl.$^2$ ................... C07C 125/04; C07C 125/06
[52] U.S. Cl. .................................... 560/132; 560/133; 560/134; 560/136; 560/137
[58] Field of Search ................... 260/479 C; 560/132, 560/133, 134, 136, 137

[56] References Cited

FOREIGN PATENT DOCUMENTS

| 956,661 | 2/1962 | United Kingdom ............. 260/479 C |
| 1,203,927 | 5/1969 | United Kingdom ............. 260/479 C |

OTHER PUBLICATIONS

Glatthard et al., Helvetica Chimicia Acta., 1963, vol. 46, pp. 795–804.

*Primary Examiner*—Natalie Trousof
*Assistant Examiner*—Jane T. Fan
*Attorney, Agent, or Firm*—Morgan, Finnegan, Pine, Foley & Lee

[57] ABSTRACT

Aromatic urethans are prepared by reacting aromatic carbonates with aliphatic amines, within an organic solvent or not. It is preferred that a stoichiometric quantity of the amine be employed to prevent the formation of urea by-products which are likely to be formed if an excess of the amine is used. The temperature should not exceed 100° C, the interval between 20° and 40° C being preferred. Nearly quantitative yields are obtained.

1 Claim, No Drawings

METHOD FOR THE PREPARATION OF AROMATIC URETHANS

This invention relates to a method for the preparation of aromatic urethans having the formula

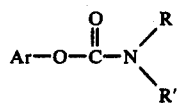

wherein Ar is a radical containing at least one aromatic group of the kind of phenyl, naphthyl, possibly substituted with alkyl, alkoxy, aryl, aryloxy, halogens, dialkylamino. R and R' are equal to one another or different and are alkyl radicals or hydrogen atoms.

It is known that the compounds in question are synthesized starting from their respective phenols and alkyl-isocyanates, or also from aryl chloroformates and amines, as can be seen in the Italian Patent Specification No. 965 506.

Such a prior method, in addition to being very intricate, involves considerable hazards on account of the toxicity of the reactants which are employed therefor.

It is likewise known that such products find a wide field of use in the industry as insecticides, a few of which are particularly interesting for their low toxicity-index.

It has now been found that it is possible to obtain such compounds by reacting aromatic carbonates with aliphatic amines, in the presence of organic solvents, or not. The reaction takes place spontaneously and quickly, even in very bland conditions until the carbonate has completely been converted, by employing stoichiometrical amounts of the amine.

An excess of the amine, or a too high temperature (above 100° C) could be conducive to the formation of a certain amount of urea as a by-product.

By way of illustration only and without limitation, a few exemplary embodiments of the method according to the invention are reported hereinafter.

EXAMPLE 1

A 500-ml flask has been charged with 107 grams of bisphenyl carbonate and 150 mls of benzene.

30 grams of pure propylamine have gradually been introduced into the mixture, the temperature being maintained in the vicinity of 40° C.

There have been obtained 86 grams of phenyl-propyl urethan with a yield of 95% approx. of theory.

EXAMPLE 2

A 500-ml flask has been charged with 160 grams of bisnaphthyl carbonate and 150 mls of dioxan.

16 grams of pure gaseous methylamine have been bubbled through the mixture during one year, the temperature being maintained at 20° C.

There have been obtained 93 grams of alpha-naphthyl-alphamethyl urethan.

EXAMPLE 3

A 500-ml flask has been charged with 140 grams of bis(4-chlorophenyl)carbonate and 150 mls of CCl₄.

16 grams of pure methylamine have been added by maintaining the temperature at 30° C.

There have been obtained 85 grams of 4-chloro-phenyl-N-methyl urethan.

What I claim is:

1. In a method for preparing aromatic urethans of the formula:

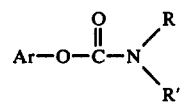

wherein Ar is selected from phenyl, naphthyl and alkyl-, aryl-, aryloxy-, halogen- and dialkylamino- substituted derivatives thereof and R and R' are each selected from hydrogen or lower alkyl comprising reacting an aromatic carbonate of the formula:

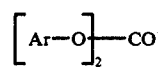

with an aliphatic amine of the formula:

wherein Ar, R and R' are as defined above,
  the improvement which consists of effecting the reaction, optionally in the presence of an organic solvent, between 20° and 100° C and employing stoichiometric amounts of said aliphatic amine thereby preventing formation of undesired urea by-product.

* * * * *